(12) United States Patent
Sakaguchi

(10) Patent No.: US 11,626,209 B2
(45) Date of Patent: Apr. 11, 2023

(54) DIAGNOSIS SUPPORT APPARATUS, DIAGNOSIS SUPPORT SYSTEM, DIAGNOSIS SUPPORT METHOD, AND NON-TRANSITORY STORAGE MEDIUM

(71) Applicant: Canon Medical Systems Corporation, Otawara (JP)

(72) Inventor: Takuya Sakaguchi, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 191 days.

(21) Appl. No.: 16/561,746

(22) Filed: Sep. 5, 2019

(65) Prior Publication Data
US 2020/0082943 A1 Mar. 12, 2020

(30) Foreign Application Priority Data

Sep. 6, 2018 (JP) .............................. JP2018-167023

(51) Int. Cl.
*G16H 50/20* (2018.01)
*G06N 20/00* (2019.01)
*G16H 10/60* (2018.01)

(52) U.S. Cl.
CPC ............. *G16H 50/20* (2018.01); *G06N 20/00* (2019.01); *G16H 10/60* (2018.01)

(58) Field of Classification Search
CPC ......... G16H 50/20; G16H 10/60; G06N 20/00
See application file for complete search history.

(56) References Cited

U.S. PATENT DOCUMENTS

| 7,536,044 | B2 * | 5/2009 | Zhou ..................... | G06V 10/754 |
| | | | | 382/128 |
| 7,650,321 | B2 * | 1/2010 | Krishnan ............... | G16H 50/20 |
| | | | | 706/20 |
| 7,653,227 | B2 * | 1/2010 | Krishnan ............... | G16H 50/20 |
| | | | | 382/128 |
| 7,949,167 | B2 * | 5/2011 | Krishnan ............... | G16H 50/70 |
| | | | | 382/128 |

(Continued)

FOREIGN PATENT DOCUMENTS

| JP | 2013-10009 A | 1/2013 |
| JP | 2016-99656 A | 5/2016 |
| WO | 2018/098039 A1 | 5/2018 |

OTHER PUBLICATIONS

Office Action dated Apr. 19, 2022, issued in corresponding Japanese patent application No. 2018-167023.

*Primary Examiner* — Jay M. Patel
(74) *Attorney, Agent, or Firm* — Oblon, McClelland, Maier & Neustadt, L.L.P.

(57) ABSTRACT

According to one embodiment, a diagnosis support apparatus includes processing circuitry. The processing circuitry executes identification processing by using medical information as an input to output a first identification result and a first identification reason for providing the first identification result. The processing circuitry modifies the identification processing to refrain from outputting the first identification reason in response to an instruction to reject the first identification reason. The processing circuitry executes the modified identification processing by using the medical information as an input to output a second identification result and a second identification reason for providing the second identification result.

14 Claims, 11 Drawing Sheets

(56) References Cited

U.S. PATENT DOCUMENTS

| | | | | |
|---|---|---|---|---|
| 7,965,869 | B2* | 6/2011 | Zhou | G06T 7/251 |
| | | | | 382/128 |
| 8,494,238 | B2* | 7/2013 | Zhou | G06K 9/00 |
| | | | | 382/128 |
| 2005/0049497 | A1* | 3/2005 | Krishnan | G16H 50/20 |
| | | | | 600/437 |
| 2005/0147303 | A1* | 7/2005 | Zhou | G06V 10/754 |
| | | | | 382/128 |
| 2005/0209519 | A1* | 9/2005 | Krishnan | G16H 50/20 |
| | | | | 600/437 |
| 2006/0184475 | A1* | 8/2006 | Krishnan | G16H 50/20 |
| | | | | 706/20 |
| 2007/0118399 | A1* | 5/2007 | Avinash | G16H 40/20 |
| | | | | 705/2 |
| 2009/0310836 | A1* | 12/2009 | Krishnan | G06T 7/0012 |
| | | | | 382/128 |
| 2011/0188706 | A1* | 8/2011 | Zhou | G06K 9/00 |
| | | | | 382/103 |
| 2012/0051608 | A1* | 3/2012 | Avinash | G06T 7/11 |
| | | | | 382/128 |
| 2014/0324469 | A1* | 10/2014 | Reiner | G16H 50/70 |
| | | | | 705/3 |
| 2016/0140305 | A1* | 5/2016 | Takeyama | G16Z 99/00 |
| | | | | 705/3 |
| 2016/0267222 | A1* | 9/2016 | Larcom | G16H 30/20 |
| 2018/0137250 | A1* | 5/2018 | Ding | G16H 20/00 |
| 2020/0027554 | A1* | 1/2020 | Boroczky | G16H 10/60 |
| 2020/0311572 | A1* | 10/2020 | Baker | G06N 20/20 |

* cited by examiner

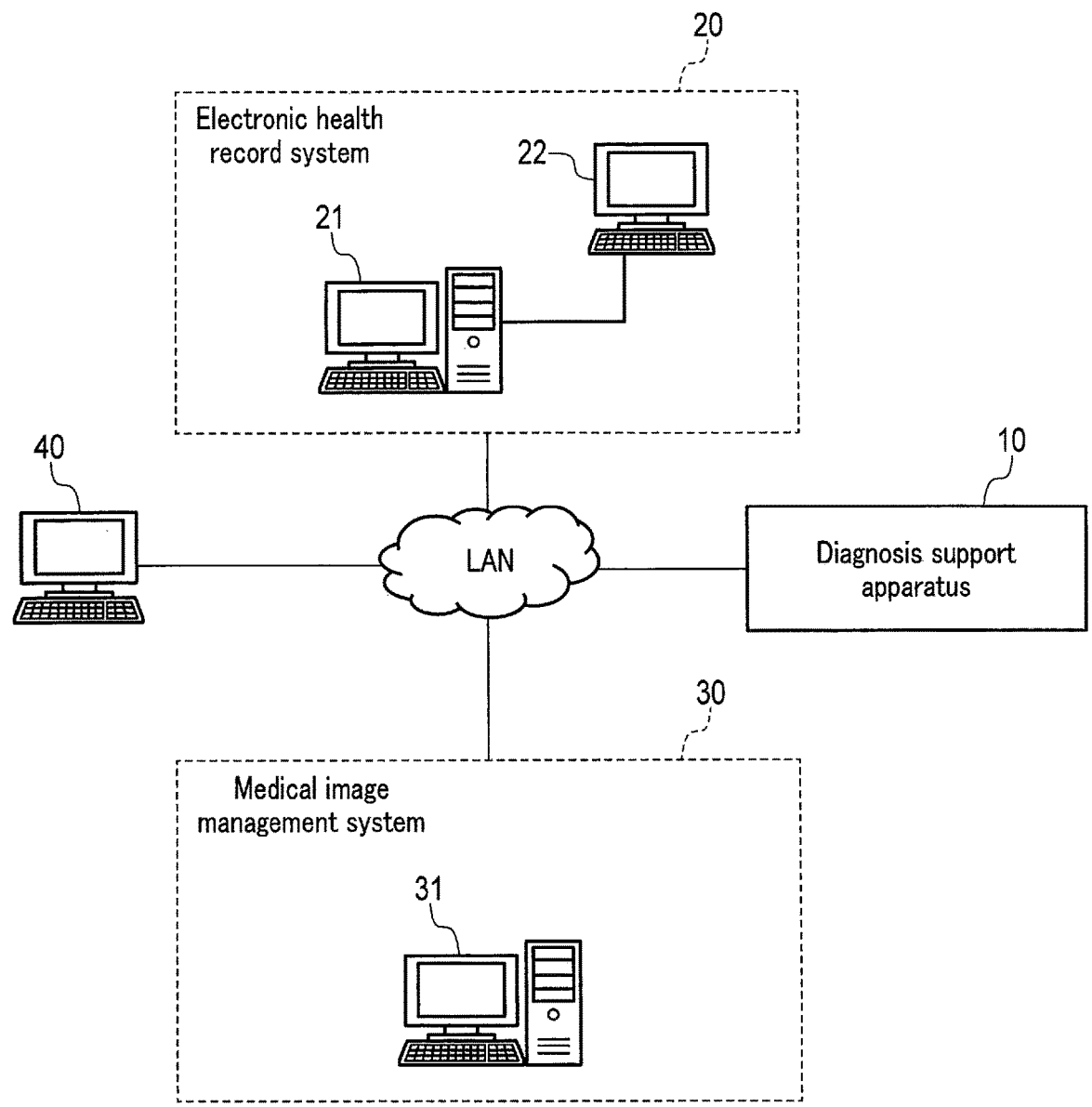
F I G. 1

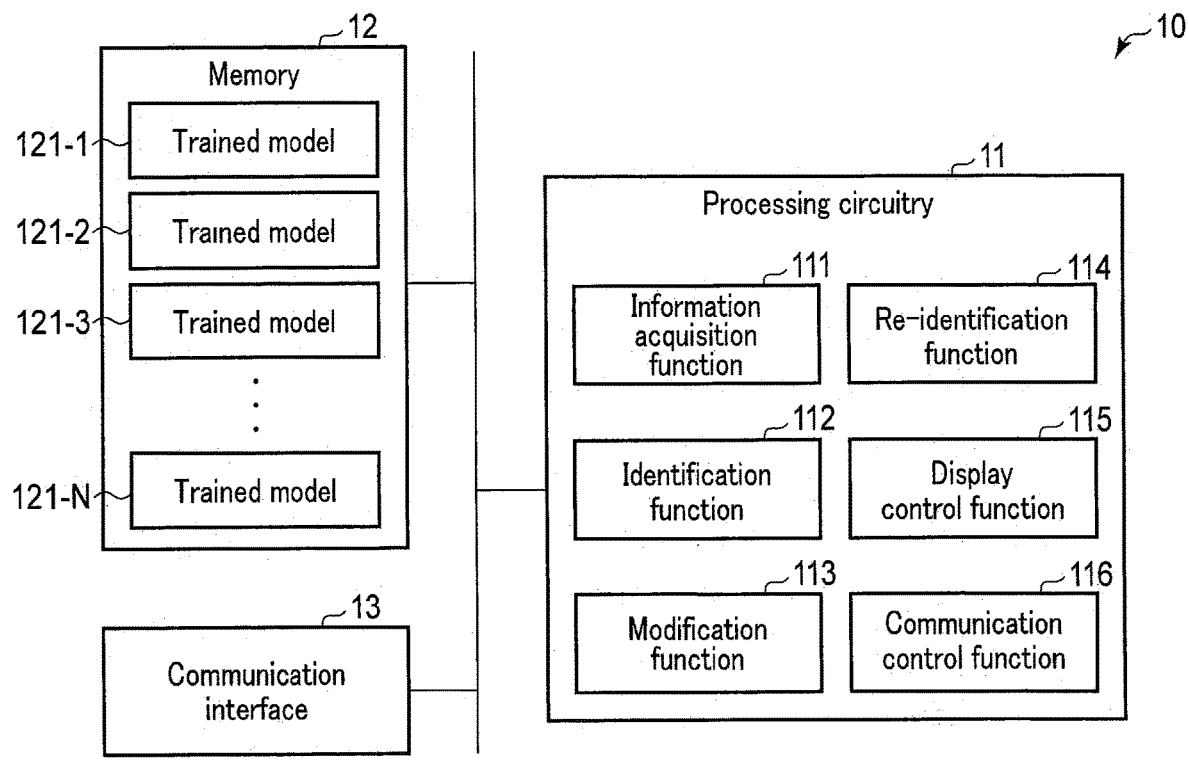
F I G. 2
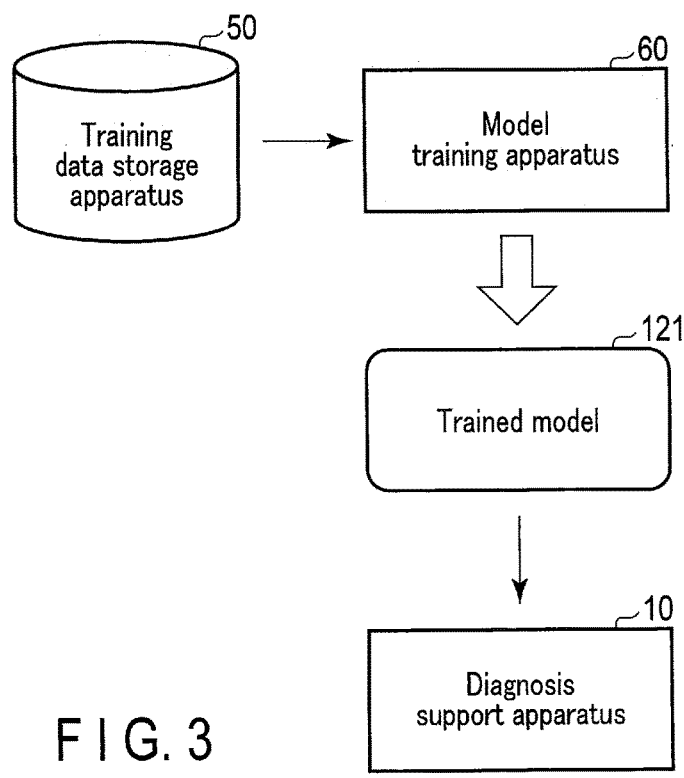
F I G. 3

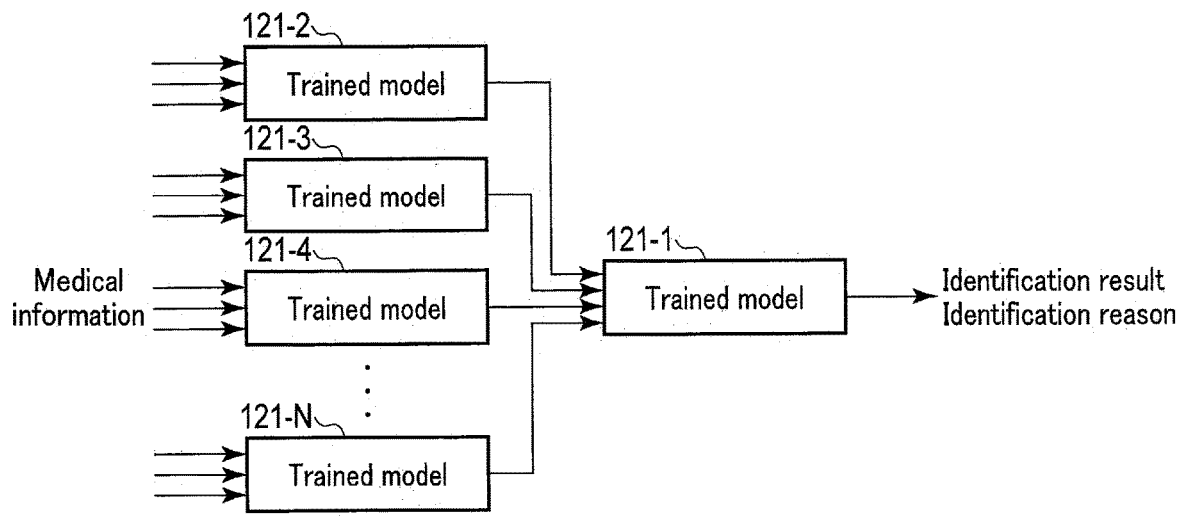
F I G. 6
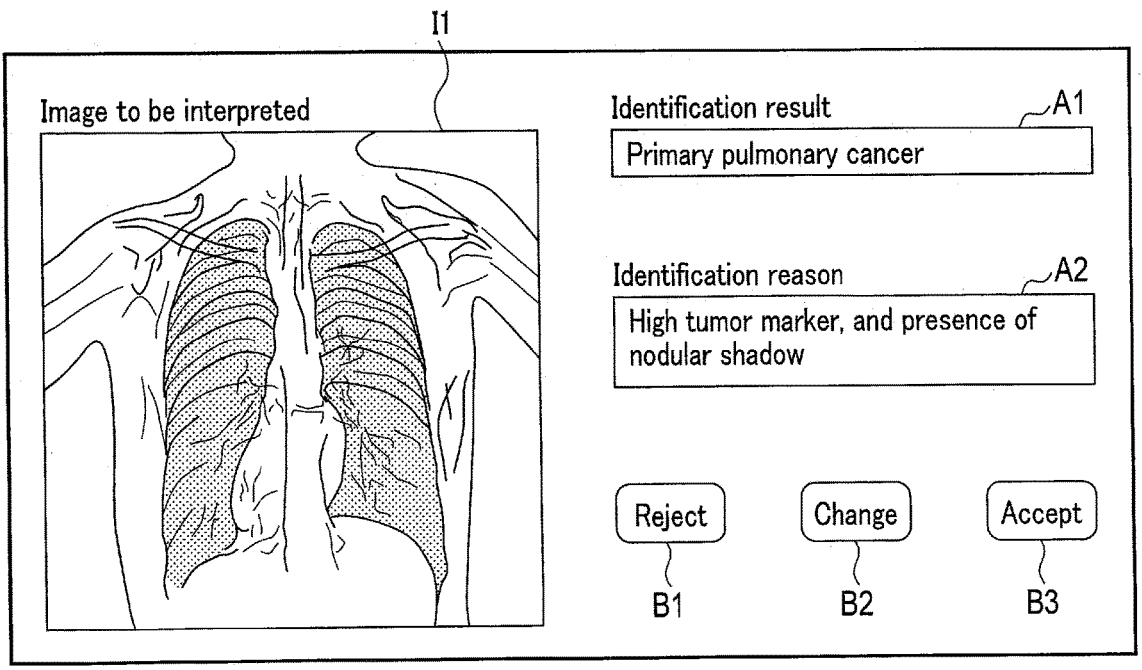
F I G. 7

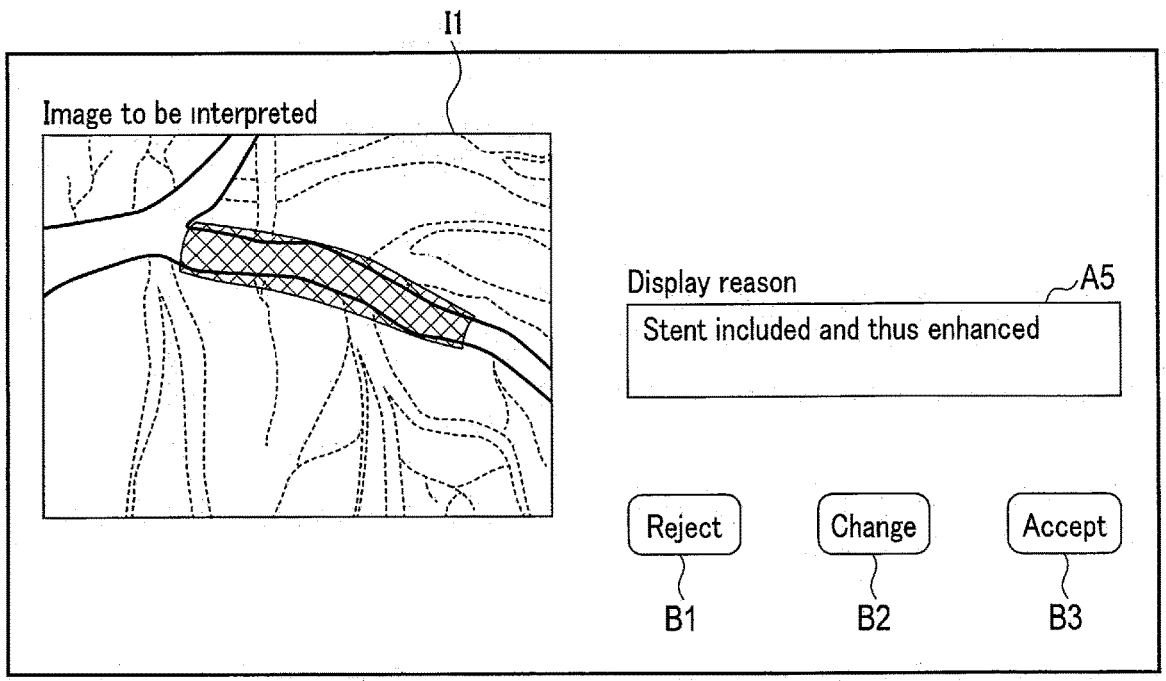
F I G. 16
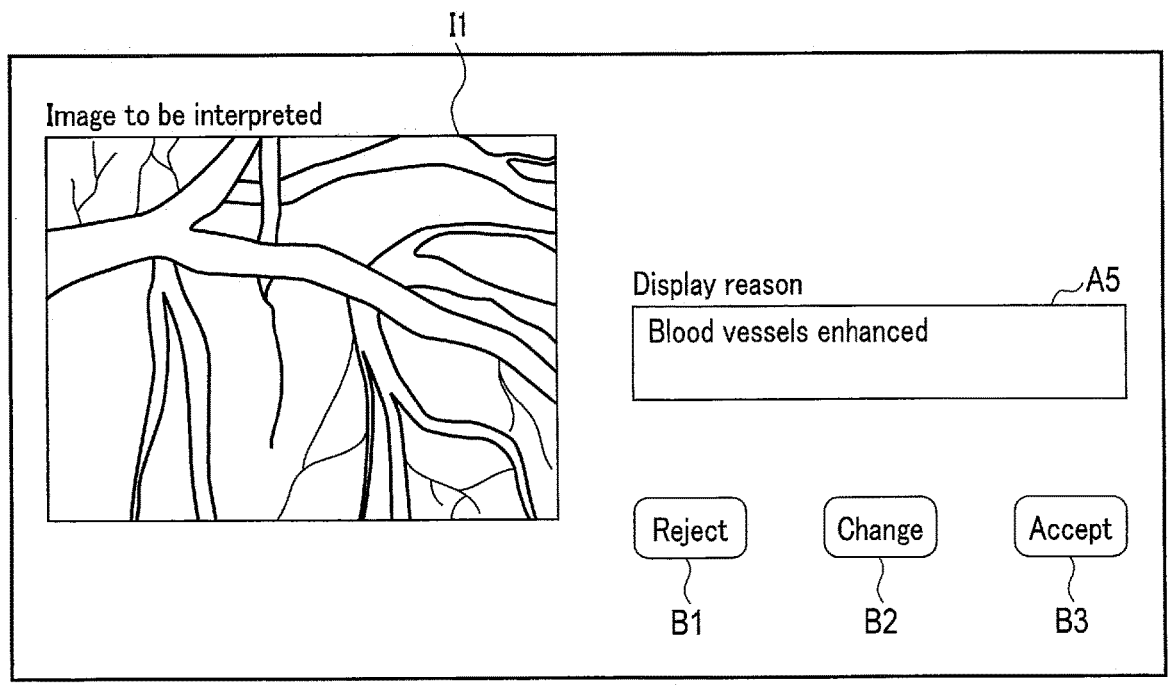
F I G. 17

DIAGNOSIS SUPPORT APPARATUS, DIAGNOSIS SUPPORT SYSTEM, DIAGNOSIS SUPPORT METHOD, AND NON-TRANSITORY STORAGE MEDIUM

CROSS-REFERENCE TO RELATED APPLICATIONS

This application is based upon and claims the benefit of priority from the prior Japanese Patent Application No. 2018-167023, filed Sep. 6, 2018, the entire contents of which are incorporated herein by reference.

FIELD

Embodiments described herein relate generally to a diagnosis support apparatus, a diagnosis support system, a diagnosis support method, and a non-transitory storage medium.

BACKGROUND

In recent years, development of a medical artificial intelligence (AI) program that outputs an identification result based on examination data has been advanced. Doctors desire to determine whether to adopt an identification result based on understanding of why the medical AI program has output the identification result. In response to the doctors' desire, a medical AI program that outputs an identification result as well as an identification reason for providing the identification result is beginning to be developed.

However, when a doctor is not convinced of the identification reason for providing the identification result, the doctor needs to select whether to adopt the output identification result with uncertainty or reject the identification result based on their own conviction.

BRIEF DESCRIPTION OF THE DRAWINGS

FIG. 1 is a block diagram showing a functional configuration of a hospital information system including a diagnosis support apparatus according to the present embodiment.

FIG. 2 is a block diagram showing a functional configuration of the diagnosis support apparatus shown in FIG. 1.

FIG. 3 is a diagram showing a configuration of a medical information processing system that generates a trained model.

FIG. 6 is a diagram showing a configuration of an identification device realized by trained models.

FIG. 7 is a diagram showing a screen displayed on the communication terminal shown in FIG. 1.

FIG. 16 is a diagram showing a screen displayed on the communication terminal shown in FIG. 1.

FIG. 17 is a diagram showing a screen re-displayed on the communication terminal shown in FIG. 1.

DETAILED DESCRIPTION

Figure 4:
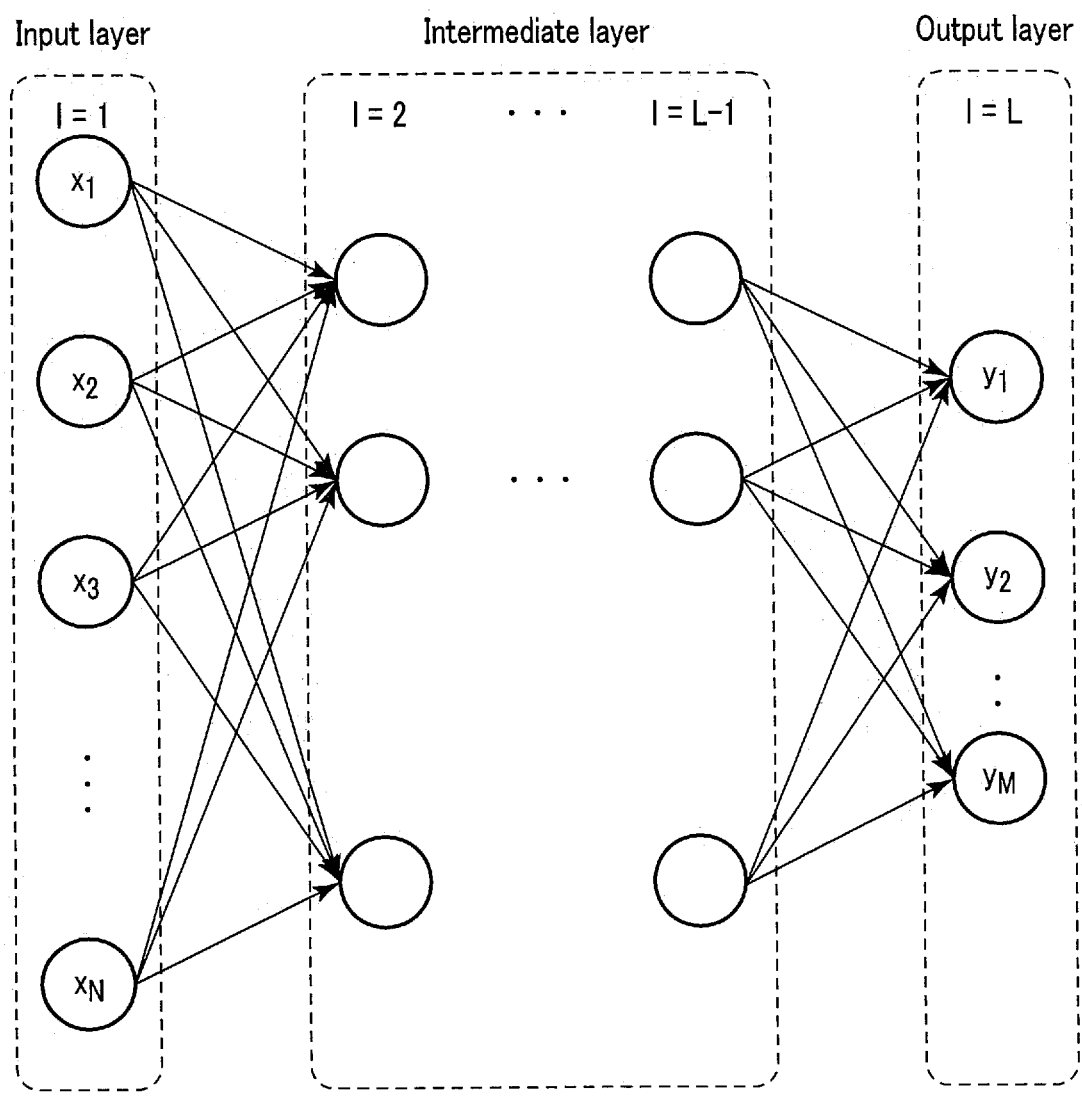
FIG. 4 is a diagram showing a configuration of a multilayer network according to the present embodiment.

In general, according to one embodiment, a diagnosis support apparatus includes processing circuitry. The processing circuitry executes identification processing by using medical information as an input to output a first identification result and a first identification reason for providing the first identification result. The processing circuitry modifies the identification processing to refrain from outputting the first identification reason in response to an instruction to reject the first identification reason. The processing circuitry executes the modified identification processing by using the medical information as an input to output a second identification result and a second identification reason for providing the second identification result.

Hereinafter, an embodiment will be described with reference to the drawings.

FIG. 1 is a block diagram showing an example of the functional configuration of a hospital information system including a diagnosis support apparatus 10 according to the present embodiment. The hospital information system shown in FIG. 1 includes a diagnosis support apparatus 10, an electronic health record system 20, a medical image management system (picture archiving and communication system (PACS)) 30, and a communication terminal 40. The diagnosis support apparatus 10, the electronic health record system 20, the medical image management system 30, and the communication terminal 40 are connected through an intra-hospital network, such as a local area network (LAN), in a manner enabling data communication. The connection to the intra-hospital network may be a wired connection or wireless connection. As long as security is ensured, the connection need not be necessarily made to the intra-hospital network. For example, the connection may be made to a public communication line, such as the Internet, through a virtual private network (VPN) or the like.

The electronic health record system 20 is a system that stores electronic health record data including, for example, medical examination information, patient information, and manages the stored electronic health record data. The medical examination information includes information concerning an electronic health record, such as finding information, disease name information, vital sign information, examination stage information, and information on details of treatment. The patient information includes, for example, a patient ID, a patient's name, gender, and age.

The electronic health record system 20 includes, for example, a server apparatus 21 and a communication terminal 22. The server apparatus 21 and the communication terminal 22 are connected through an intra-hospital network in a manner enabling data communication. In the electronic health record system 20, the server apparatus 21 stores medical examination information, patient information, etc., and manages the stored medical examination information, patient information, etc. For example, in response to an output request, the server apparatus 21 outputs stored medical examination information, patient information, etc. to the requester.

FIG. 1 shows, as an example, the case where the electronic health record system 20 includes only one server apparatus 21; however, the configuration of the electronic health record system 20 is not limited to this. The electronic health record system 20 may include a plurality of server apparatuses 21 as needed. For example, the server apparatus 21 may be provided for each type of managed information.

The communication terminal 22 is a terminal for medical staff, such as a doctor, to access the server apparatus 21. For example, the communication terminal 22 is operated by medical staff and requests the server apparatus 21 for information stored in the server apparatus 21.

The medical image management system 30 is a system that stores medical image data and manages the stored medical image data. The medical image management system 30 includes, for example, a server apparatus 31. In the medical image management system 30, the server apparatus 31 stores medical image data converted in accordance with, for example, the digital imaging and communication medicine (DICOM) standard, and manages the stored medical image data. For example, in response to a browsing request, the server apparatus 31 transmits stored medical image data to the requester.

FIG. 1 shows, as an example, the case where the medical image management system 30 includes only one server apparatus 31; however, the configuration of the medical image management system 30 is not limited to this. The medical image management system 30 may include a plurality of server apparatuses 31 as needed.

The communication terminal 40 is a terminal, such as a viewer, for medical staff to access a system, apparatus, etc. connected to the LAN. FIG. 1 shows the case where the communication terminal 40 is not included in the electronic health record system 20 or medical image management system 30; however, the embodiment is not limited to this. As long as medical staff can use the communication terminal 40, the communication terminal 40 may be included in either the electronic health record system 20 or the medical image management system 30.

The diagnosis support apparatus 10 is an apparatus that supports an operator, such as a doctor, in diagnosing a patient. FIG. 2 is a block diagram showing an example of the functional configuration of the diagnosis support apparatus 10 shown in FIG. 1. The diagnosis support apparatus 10 shown in FIG. 2 includes processing circuitry 11, a memory 12, and a communication interface 13. The processing circuitry 11, the memory 12, and the communication interface 13 are connected through, for example, a bus in a manner enabling communicate therebetween.

The processing circuitry 11 is a processor that functions as the nerve center of the diagnosis support apparatus 10. The processing circuitry 11 executes a program stored in, for example, the memory 12, thereby realizing a function corresponding to the program.

The memory 12 is a storage device, such as a read only memory (ROM), a random access memory (RAM), a hard disk drive (HDD), a solid state drive (SSD), or an integrated circuit storage device, which stores various information. The memory 12 may be, for example, a CD-ROM drive, a DVD drive, or a drive which reads and writes various information from and in a portable storage medium, such as a flash memory. The memory 12 need not necessarily be realized by a single storage device. For example, the memory 12 may be realized by a plurality of storage devices. Furthermore, the memory 12 may be located within another computer connected to the diagnosis support apparatus 10 through a network.

The memory 12 stores, for example, a diagnosis support program according to the present embodiment. This diagnosis support program may be, for example, stored in advance in the memory 12. Alternatively, the diagnosis support program may be stored in a non-transitory storage medium and distributed, and then read from the non-transitory storage medium and installed in the memory 12. The memory 12 stores, for example, trained models 121-1, 121-2, . . . , 121-N as an identification device generated through machine learning. The trained models 121-1 to 121-N are an example of a computation model. In the present embodiment, the trained model refers to a model generated by having a machine learning model perform machine learning in accordance with a model training program.

The trained models 121-1 to 121-N are generated, for example, as will be described below and are stored in the memory 12 of the diagnosis support apparatus 10. The trained models 121-1 to 121-N are generated in the same manner, and thus will be referred to as a trained model 121 in the following description.

FIG. 3 is a schematic diagram showing an example of the configuration of the medical information processing system which generates the trained model 121. The medical information processing system shown in FIG. 3 includes the diagnosis support apparatus 10, a training data storage apparatus 50, and a model training apparatus 60.

The training data storage apparatus 50 stores training data including a plurality of training samples. For example, the training data storage apparatus 50 is a computer with a mass-storage device incorporated therein. The training data storage apparatus 50 may also be a mass-storage device connected to a computer through a cable or a communication network in a manner enabling communication. As the storage device, a hard disk drive (HDD), a solid state drive (SSD), an integrated circuit storage device, or the like can be used as appropriate.

The model training apparatus 60 generates the trained model 121 by having a machine learning model perform machine learning in accordance with a model training program based on training data stored in the training data storage apparatus 50. In the present embodiment, the algorithm of machine learning includes, for example, discrimination analysis, logistic regression, a support vector machine, a neural network, Randomized Trees, and a subspace method. The model training apparatus 60 is a computer such as a workstation including a processor such as a central processing unit (CPU) or a graphics processing unit (GPU).

The model training apparatus 60 and the training data storage apparatus 50 may be connected through a cable or a communication network in a manner enabling communication. The training data storage apparatus 50 may be included in the model training apparatus 60. In those cases, training data is supplied from the training data storage apparatus 50 to the model training apparatus 60. The model training apparatus 60 and the training data storage apparatus 50 need not necessarily be connected in a manner enabling communication. In such a case, training data is supplied from the training data storage apparatus 50 to the model training apparatus 60 through a portable storage medium storing the training data.

The diagnosis support apparatus 10 and the model training apparatus 60 may be connected through a cable or a communication network in a manner enabling communication. The diagnosis support apparatus 10 and the model training apparatus 60 may be installed in a single computer. In those cases, the trained model 121 generated by the model training apparatus 60 is supplied to the diagnosis support apparatus 10. The diagnosis support apparatus 10 and the model training apparatus 60 need not necessarily be connected in a manner enabling communication. In such a case, the trained model 121 is supplied from the model training apparatus 60 to the diagnosis support apparatus 10 via a portable storage medium storing the trained model 121.

The trained model 121 may be supplied to the diagnosis support apparatus 10 at any point in time after manufacture of the diagnosis support apparatus 10. For example, the trained model 121 may be supplied to the diagnosis support apparatus 10 at any point in time between manufacture and installation to a medical facility or the like, or at a time of maintenance. The supplied trained model 121 is stored in the memory 12 of the diagnosis support apparatus 10.

The trained model 121 according to the present embodiment is a composite function with parameters, which is a combination of a plurality of functions, for making inference of a disease name, inference of a disease malignancy grade, prognostic prediction, or the like by using medical information, such as medical image data and non-image medical examination information, as an input. The composite function with parameters is defined by a combination of a plurality of adjustable functions and parameters. The trained model 121 according to the present embodiment may be any composite function with parameters that satisfies the above-described requirements.

For example, the trained model 121 is generated using a feedforward multi-layer network. In the present embodiment, the feedforward multi-layer network has a layered structure in which only adjacent layers are coupled to each other as shown in, for example, FIG. 4, and information is propagated in one direction from the input-layer side to the output-layer side. The multi-layer network shown in FIG. 4 is constituted by L layers including an input layer (I=1), an intermediate layer (I=2, 3, . . . , L−1), and an output layer (I=L).

When the trained model 121 is generated using the feedforward multi-layer network, the composite function with parameters is defined as, for example, a combination of a linear relationship between layers using a weighting matrix, a nonlinear relationship (or linear relationship) using an active function in each layer, and a bias. The activation function can be selected from various functions such as a logistic sigmoid function (logistic function), a hyperbolic tangent function, a linear normalization function (rectified linear unit (ReLU)), linear mapping, identity mapping, and a maxout function, depending on the purpose.

The weighting matrix and bias are referred to as a parameter of the multi-layer network. The composite function with parameters changes its form as a function, depending on how the parameters are selected. In the multi-layer network, a function capable of outputting a preferable result from the output layer can be defined by appropriately setting parameters constituting the function.

The parameters are set by execution of training using training data and an error function. For example, the training data is a set D (n=1, . . . , S) of training samples (xn, dn), each of which consists of a predetermined input xn and a desirable result (correct output) dn corresponding to the input. The error function is a function representing the closeness between the correct output dn and the output from the multi-layer network in which xn is input. The error function typically includes a square error function, a maximum-likelihood estimation function, a crossover entropy function, etc. A function selected as the error function depends on the problem which the multi-layer network deals with (for example, a regression problem, a binary problem, or a multi-class classification problem). As the parameters, for example, values that minimize the error function are determined for each training sample. In order to suppress the computation amount at the time of determining the parameters, a backward propagation method may be used.

Specifically, the model training apparatus 60 according to the present embodiment performs machine learning based on training data consisting of inputs of a predetermined feature amount in medical image data and a predetermined feature amount in non-medical image data such as medical examination information and a correct output of a determined disease name. The predetermined feature amount in medical image data is, for example, a texture feature amount, such as a mean value, kurtosis, skewness, or gray-level co-occurrence matrix (GLCM). The predetermined feature amount in non-image data is, for example, a result of a blood test, a smoking history, gender, family information, or a result of genomic analysis. The model training apparatus 60 generates trained models 121-2 to 121-N for identifying a disease name based on, for example, an input predetermined feature amount in medical image data and predetermined feature amount in non-image data such as medical examination information.

The parameters of trained models 121-2 to 121-N may be set, for example, by using different training data. For example, the parameters of at least one of the trained models 121-2 to 121-N may be set by using training data concerning a specific disease. Alternatively, the parameters of at least one of the trained models 121-2 to 121-N may be set by using training data concerning a specific site. Accordingly, different identification results are output from trained models 121-2 to 121-N.

The correct output of training data used when generating trained models 121-2 to 121-N is not limited to the determined disease name. The model training apparatus 60 may generate trained models 121-2 to 121-N by performing machine learning based on training data having a diagnostic result of a malignancy grade of a disease as the correct output.

The model training apparatus 60 according to the present embodiment also performs machine learning based on, for example, training data consisting of inputs of identification results output from trained models 121-2 to 121-N and identification reasons for providing the results and correct outputs of a determined disease name and a reason for the diagnosis. For example, the model training apparatus 60 generates trained model 121-1 which outputs a disease name and a reason for the diagnosis in response to input of identification results and identification reasons for providing the results output from trained models 121-2 to 121-N.

The communication interface 13 shown in FIG. 2 performs data communication between the electronic health record system 20, the medical image management system 30, and the communication terminal 40, which are connected through an intra-hospital network. The communication interface 13 performs data communication in accordance with, for example, a known standard which is set in advance. The communication interface 13 performs communication with the electronic health record system 20 in accordance with, for example, HL7. The communication interface 13 performs communication with the medical image management system 30 in accordance with, for example, DICOM.

The diagnosis support apparatus 10 may include an input interface. The input interface receives various input operations from a user, converts the received input operation into an electrical signal, and outputs the electrical signal to the processing circuitry 11. The input interface is connected to an input device, such as a mouse, a keyboard, a trackball, a switch, a button, a joystick, a touch-pad, or a touch panel to which an instruction is input by a user touching the operation screen. The input device connected to the input interface may be an input device provided in another computer connected through a network, etc.

The diagnosis support apparatus 10 may include a display. The display displays various information in accordance with an instruction from the processing circuitry 11. The display may display, for example, a graphical user interface (GUI) for receiving various operations from a user. As the display, any display, such as a cathode ray tube (CRT) display, a liquid crystal display, an organic EL display, an LED display, or a plasma display, may be used as appropriate.

The processing circuitry 11 shown in FIG. 2 executes a diagnosis support program stored in the memory 12, thereby realizing a function corresponding to the program. For example, by executing a diagnosis support program, the processing circuitry 11 realizes an information acquisition function 111, an identification function 112, a modification function 113, a re-identification function 114, a display control function 115, or a communication control function 116. Described in the present embodiment is the case where a single processor realizes the information acquisition function 111, the identification function 112, the modification function 113, the re-identification function 114, the display control function 115, and the communication control function 116; however, the embodiment is not limited to such a case. A plurality of independent processors may constitute processing circuitry in combination, and execute respective programs to realize the information acquisition function 111, the identification function 112, the modification function 113, the re-identification function 114, the display control function 115, and the communication control function 116.

The information acquisition function 111 is a function of acquiring medical information to be input into trained models 121-2 to 121-N from data stored in the hospital information system. For example, with the information acquisition function 111, the processing circuitry 11 reads patient information on a patient designated by an operator and medical examination information on the patient from the electronic health record system 20. The processing circuitry 11 also reads medical image data stored in connection with the patient designated by the operator from the medical image management system 30. The medical image data includes, for example, ultrasound image data, computed tomography (CT) image data, X-ray image data, magnetic resonance imaging (MRI) image data, and positron emission computed tomography (PET) image data.

The identification function 112 is a function of using trained models 121-1 to 121-N with the acquired medical information used as an input, and outputting identification results and reasons for providing the results. For example, with the identification function 112, the processing circuitry 11 extracts predetermined feature amounts from patient information and medical examination information read from the electronic health record system 20 and medical image data read from the medical image management system 30. The processing circuitry 11 inputs the extracted feature amounts into trained models 121-2 to 121-N, and generates identification results, such as a disease name or a malignancy grade of the disease.

The processing circuitry 11 generates a reason for providing the identification result for each of trained models 121-2 to 121-N. The processing circuitry 11 calculates a degree of contribution of each of the input feature amounts in accordance with, for example, the degree of importance for obtaining the identification result for each of trained models 121-2 to 121-N. The degree of contribution is calculated by, for example, a method of performing calculation based on the input and output, only, and a method of performing an inverse calculation using a weight or the like set in the trained model. The processing circuitry 11 generates an identification reason based on the calculated degrees of contribution.

The processing circuitry 11 inputs the identification results and identification reasons output from trained models 121-2 to 121-N into trained model 121-1, and outputs an identification result and an identification reason as the final outputs.

The modification function 113 is a function of changing the identification processing. For example, with the modification function 113, the processing circuitry 11 changes the setting of trained models 121-1 to 121-N in accordance with an instruction to change the identification reason which is input by the operator.

The re-identification function 114 is a function of executing the modified identification processing and thereby re-outputting an identification result and an identification reason for providing the identification result. For example, with the re-identification function 114, the processing circuitry 11 inputs medical information into trained models 121-1 to 121-N after the setting is changed, and re-outputs an identification result and an identification reason.

The display control function 115 is a function of controlling a display regarding outputs of trained models 121-1 to 121-N. For example, with the display control function 115, the processing circuitry 11 generates image data for displaying an identification result and identification reason output by the identification function 112. The processing circuitry 11 also displays a GUI for providing an instruction to change the identification reason.

The communication control function 116 is a function of controlling communication between the electronic health record system 20, the medical image management system 30, and the communication terminal 40. For example, with the communication control function 116, the processing circuitry 11 accesses the electronic health record system 20 and the medical image management system 30, and reads medical information designated by the information acquisition function 111 from the electronic health record system 20 and the medical image management system 30. The processing circuitry 11 also accesses the communication terminal 40 and transmits the image data generated by the display control function 115 to the communication terminal 40 through a LAN.

Next, the diagnosis support operation by the diagnosis support apparatus 10 configured as described above will be described while following the processing procedure of the processing circuitry 11.

Figure 5:
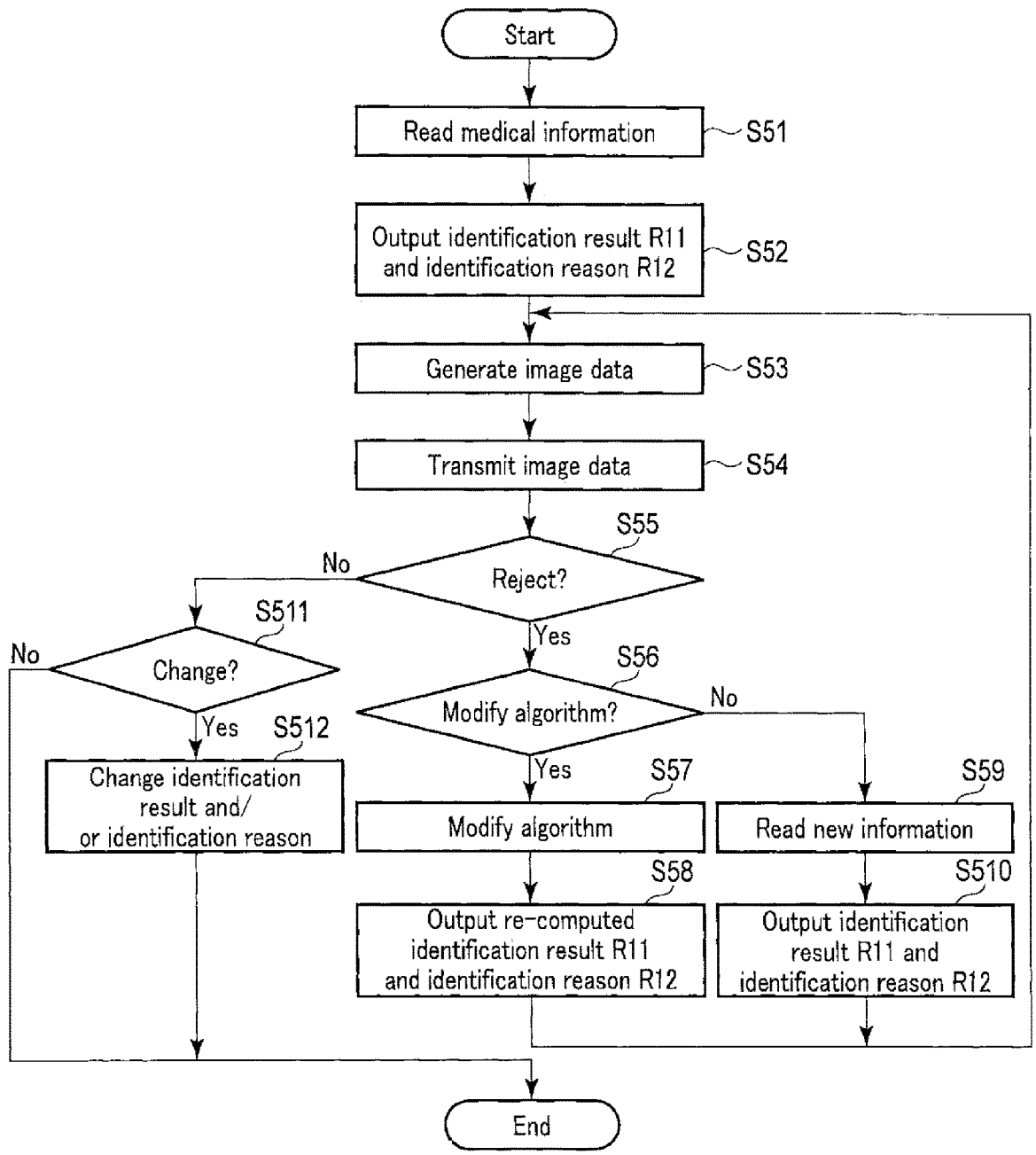
FIG. 5 is a flowchart showing operations performed when the processing circuitry shown in FIG. 2 executes identification processing using trained models.

FIG. 5 is a flowchart showing an example of operations performed when the processing circuitry 11 shown in FIG. 2 executes identification processing using trained models 121-1 to 121-N. The description of FIG. 5 will be provided while taking, as an example, the case where the identification device realized by trained models 121-1 to 121-N is configured as shown in FIG. 6. In the case shown in FIG. 6, medical information is input into trained models 121-2 to 121-N, and identification results R21 to RN1 and identification reasons R22 to RN2 are output. Then, the identification results R21 to RN1 and identification reasons R22 to RN2 output from trained models 121-2 to 121-N are input into trained model 121-1, and identification result R11 and identification reason R12 are output as final outputs.

First, upon receipt of an instruction to start identification processing for a designated patient from an operator who operates the communication terminal 40, the processing circuitry 11 of the diagnosis support apparatus 10 reads a diagnosis support program from the memory 12, and executes the read diagnosis support program. When the processing circuitry 11 executes the diagnosis support program, processing shown in FIG. 5 is started.

In FIG. 5, the processing circuitry 11 executes the information acquisition function 111. By executing the information acquisition function 111, the processing circuitry 11 reads, from the electronic health record system 20 and medical image management system 30, medical information to be input into trained models 121-2 to 121-N for the patient designated by the operator (step S51). Namely, the processing circuitry 11, for example, reads patient information and medical examination information on the designated patient from the electronic health record system 20, and reads medical image data on the designated patient from the medical image management system 30.

Upon acquisition of medical information, the processing circuitry 11 executes the identification function 112. By executing the identification function 112, the processing circuitry 11 outputs identification result R11 based on the read patient information, medical examination information, and medical image data, and identification reason R12 for providing the result (step S52).

Specifically, the processing circuitry 11 extracts feature amounts set for trained model 121-2, for example, at least some of a result of a blood test, a smoking history, gender, family, a result of genomic analysis, etc., from the patient information and medical examination information read from the electronic health record system 20. The processing circuitry 11 also extracts feature amounts set for trained model 121-2, for example, texture feature amounts such as a mean value, kurtosis, skewness, and GLCM, from the medical image data read from the medical image management system 30.

Specifically, let us assume that trained model 121-2 is, for example, a model for identifying a pulmonary disease name and a malignancy grade of the disease. When the medical image data input into the trained model 121-2 is CT image data, the processing circuitry 11 executes, for example, existing contour extraction processing and pattern matching processing to extract at least some of the size of a pulmonary nodule, a mean value of CT values of a pulmonary nodule, a ratio (such as a volume ratio) between a solid opacity and a ground-glass opacity, a doubling time of a pulmonary nodule, luminance distribution (such as kurtosis and skewness) of a pulmonary nodule, GLCM, etc. from the CT image data as feature amounts.

When the input medical image data is MRI image data, the processing circuitry 11 extracts, for example, the size of a pulmonary nodule in the MRI image data acquired by a predetermined sequence from the MRI image as a feature amount. When the input medical image data is PET image data, the processing circuitry 11 extracts, for example, the size of a region where the standardized uptake value (SUV) value is high in the PET image data as a feature amount.

When the input medical image data is X-ray image data, the processing circuitry 11 extracts, for example, at least some of the size of a pulmonary nodule, luminance distribution (such as kurtosis and skewness) of a pulmonary nodule, etc. as feature amounts. The feature amounts regarding medical image data are not limited to the above.

After extracting feature amounts from medical information, the processing circuitry 11 inputs the extracted feature amounts into trained model 121-2, and generates an output signal. Namely, the processing circuitry 11 inputs the feature amounts extracted from patient information, medical examination information, and medical image data into trained model 121-2 and generates identification result R21, such as a disease name and a malignancy grade of the disease. The processing circuitry 11 generates identification reason R22 for outputting the identification result from trained model 121-2 based on, for example, the degrees of contribution of the input feature amounts.

In parallel with the input of the feature amounts into trained model 121-2, the processing circuitry 11 inputs the feature amounts into trained models 121-3 to 121-N. In response to the input of the feature amounts into trained models 121-3 to 121-N, identification results R31 to RN1 are output from the respective trained models 121-3 to 121-N. The processing circuitry 11 generates identification reasons R32 to RN2 for outputting the identification results from trained models 121-3 to 121-N based on, for example, the degrees of contribution of the input feature amounts.

In response to the output of identification results R21 to RN1 and identification reasons R22 to RN2 from trained models 121-2 to 121-N, the processing circuitry 11 inputs the output identification results R21 to RN1 and identification reasons R22 to RN2 into trained model 121-1. In response to the input of identification results R21 to RN1 and identification reasons R22 to RN2 into trained model 121-1, for example, one of the input identification results and one of the input identification reasons are output as identification result R11 and identification reason R12.

In response to the output of identification result R11 and identification reason R12 from trained model 121-1, the processing circuitry 11 executes the display control function 115. By executing the display control function 115, the processing circuitry 11 generates image data for displaying identification result R11 and identification reason R12 (step S53). After generating image data, the processing circuitry 11 executes the communication control function 116. By executing the communication control function 116, the processing circuitry 11 accesses the communication terminal 40 through a LAN, and transmits the generated image data to the communication terminal 40 (step S54). The communication terminal 40 displays the received image data.

FIG. 7 is a schematic diagram showing an example of the screen displayed on the communication terminal 40. In the example shown in FIG. 7, medical image I1 is displayed on the left side, and area A1 showing identification result R11 and area A2 showing identification reason R12 are displayed on the right side. Area A1 shows "primary pulmonary cancer" as identification result R11, and area A2 shows "high tumor marker, and presence of nodular shadow" as identification reason R12.

Below area A2, buttons B1 to B3 are displayed as a GUI. Button B1 is a button for rejecting the identification reason R12 shown in area A2. Button B2 is a button for changing the identification result R11 shown in area A1 and/or the identification reason R12 shown in area A2. Button B3 is a button for accepting the identification result R11 shown in area A1 and the identification reason R12 shown in area A2.

When the identification reason R12 shown in area A2 differs from the reason envisaged by the operator, the operator selects button B1 on the communication terminal 40. For example, when the operator is not convinced of the reason "high tumor marker, and presence of nodular shadow", the operator selects button B1. When button B1 is selected by the operator on the communication terminal 40, the communication terminal 40 transmits an instruction to reject the identification reason R12 shown in area A2 to the diagnosis support apparatus 10.

Figure 8:
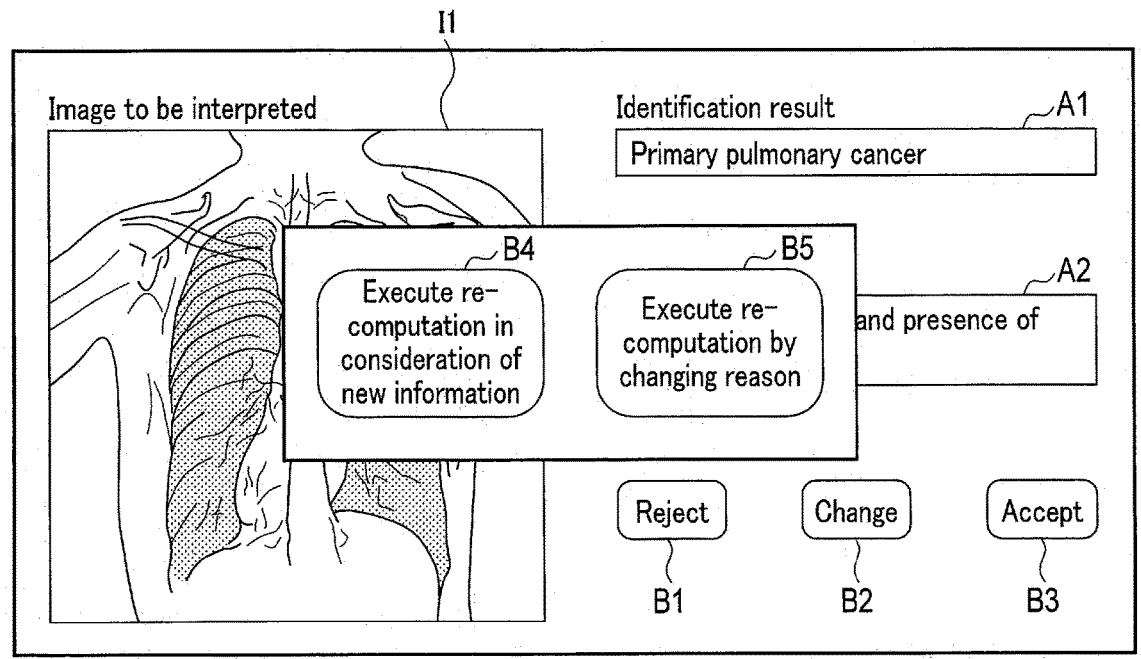
FIG. 8 is a diagram showing a screen to receive a selection of whether to modify an algorithm on the communication terminal shown in FIG. 1.

After transmitting image data to the communication terminal 40, the processing circuitry 11 of the diagnosis support apparatus 10 awaits an instruction transmitted from the communication terminal 40. Upon receipt of the instruction to reject the identification reason R12 shown in area A2 (Yes in step S55), the processing circuitry 11 causes the communication terminal 40 to display a screen to receive a selection of whether or not to modify the algorithm of identification processing. FIG. 8 is a schematic diagram showing an example of the screen to receive a selection of whether or not to modify the algorithm. FIG. 8 shows button B4 and button B5. Button B4 is a button for executing computation of an identification result and an identification reason in consideration of new information. Button B5 is a button for executing again computation of an identification result and an identification reason so that a reason different from identification reason R12 is output. Namely, button B5 is a button for receiving a selection of whether or not to modify the algorithm of trained models 121-1 to 121-N. Button B4 for executing re-computation in consideration of new information need not necessarily be displayed.

When button B5 is selected by the operator on the communication terminal 40, the communication terminal 40 transmits to the diagnosis support apparatus 10 an instruction to execute again computation of an identification result and an identification reason by modifying the algorithm of trained models 121-1 to 121-N. When the instruction is input (Yes in step S56), the processing circuitry 11 of the diagnosis support apparatus 10 executes the modification function 113.

Figure 9:
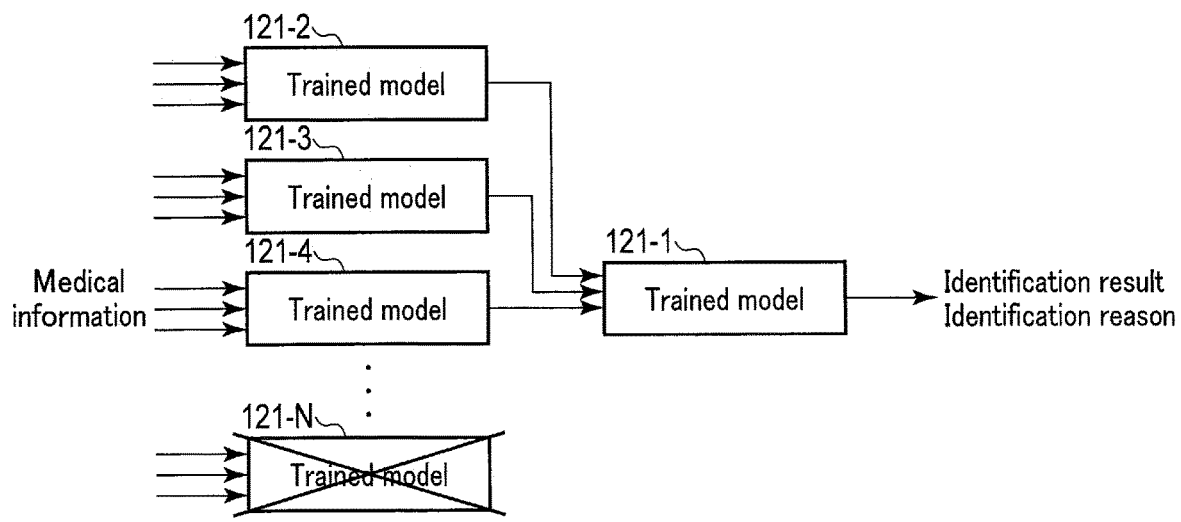
FIG. 9 is a diagram showing a modification of the algorithm of trained models shown in FIG. 6.

By executing the modification function 113, the processing circuitry 11 modifies the algorithm of trained models 121-1 to 121-N to exclude the identification reason rejected by the operator (step S57) For example, let us assume that identification result RN1 and identification reason RN2 output from trained model 121-N are selected by trained model 121-1 and output as identification result R11 and identification reason R12. The processing circuitry 11 refrains from executing identification processing using trained model 121-N, which has output identification reason RN2, for example, as shown in FIG. 9. If there is a trained model other than trained model 121-N which has output the same identification reason as the identification reason R12 rejected by the operator, the processing circuitry 11 also refrains from executing identification processing using that trained model, although it is not shown in FIG. 9.

The processing to modify the algorithm is not limited to the processing shown in FIG. 9. For example, the processing circuitry 11 may change the connection between trained model 121-1 and trained models 121-2 to 121-N so that the output from the trained model that has output the same identification reason as the identification reason R12 rejected by the operator is not input to trained model 121-1.

Alternatively, the processing circuitry 11 may lower the priority of the identification result and identification reason output from the trained model that has output the same identification reason as the identification reason R12 rejected by the operator.

After modifying the algorithm of trained models 121-1 to 121-N, the processing circuitry 11 executes the re-identification function 114. By executing the re-identification function 114, the processing circuitry 11 inputs the feature amounts extracted from medical information into the trained models after algorithm modification, and re-outputs an identification result and an identification reason (step S58). According to the example shown in FIG. 9, the processing circuitry 11 inputs the feature amounts extracted from medical information into trained models 121-2 to 121-(N−1), and outputs identification results R21 to R(N−1)1 and identification reasons R22 to R (N−1) 2. The processing circuitry 11 inputs the identification results R21 to R(N−1)1 and identification reasons R22 to R (N−1) 2 into trained model 121-1, and outputs one of the input identification results and one of the input identification reasons as identification result R11 and identification reason R12.

In response to the output of identification result R11 and identification reason R12 from trained model 121-1, the processing circuitry 11 proceeds to step S53 and generates image data, and transmits the image data to the communication terminal 40 in step S54. The communication terminal 40 displays the received image data.

Figure 10:
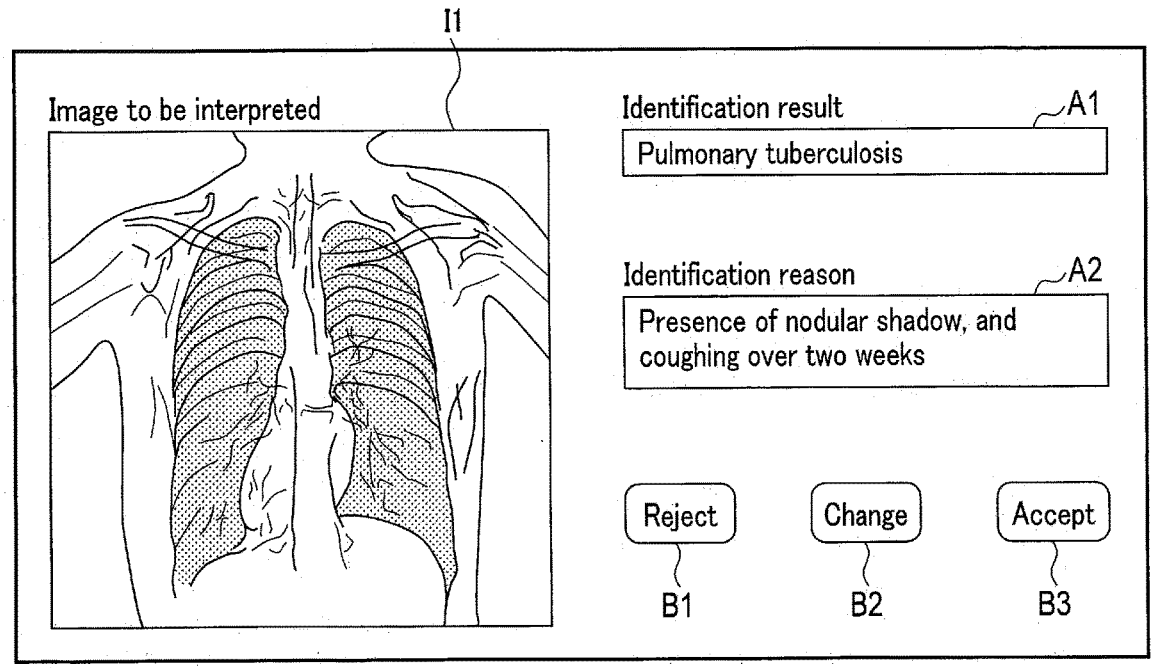
FIG. 10 is a diagram showing a screen re-displayed on the communication terminal shown in FIG. 1.

FIG. 10 is a schematic diagram showing an example of the screen re-displayed on the communication terminal 40. In the example shown in FIG. 10, re-output identification result R11 is shown in area A1, and re-output identification reason R12 is shown in area A2. Accordingly, identification reason R12 different from the identification reason rejected by the operator is shown, and identification result R11 which is identified in accordance with the identification reason R12 is shown. Namely, area A2 shown in FIG. 10 shows "presence of nodular shadow, and coughing over two weeks", which is different from "high tumor marker, and presence of nodular shadow" shown in FIG. 7. Meanwhile, area A1 shown in FIG. 10 shows "pulmonary tuberculosis" derived from the reason "presence of nodular shadow, and coughing over two weeks".

If button B4 shown in FIG. 8 is selected by the operator after the reject button B1 shown in FIG. 7 is selected, the communication terminal 40 transmits to the diagnosis support apparatus 10 an instruction to execute computation of an identification result and an identification reason in consideration of new information. After selecting button B4, the operator also selects information to be newly added. The information to be newly added is, for example, information not included in medical information read from the electronic health record system 20 and the medical image management system 30. For example, when patient information does not initially include a smoking history of the patient, the smoking history is newly input. When medical examination information does not include past examination information, information such as having colon cancer 10 years ago is newly input. When medical image data does not include MRI image data, newly-obtained MRI image data is selected.

When an instruction to execute identification processing in consideration of new information is received, and new information is selected by the operator (No in step S56), the processing circuitry 11 of the diagnosis support apparatus 10 executes the identification function 112. By executing the identification function 112, the processing circuitry 11 reads, from the electronic health record system 20 and/or medical image management system 30, new information selected by the operator (step S59). The processing circuitry 11 outputs identification result R11 and identification reason R12 for providing the result based on the patient information, medical examination information, and medical image data read in step S51 and newly-read information (step S510), and proceeds to step S53.

When determining that the identification result in area A1 and/or identification reason in area A2 shown in FIG. 7 should be changed, the operator selects button B2 on the communication terminal 40. For example, when the operator determines that a minor change should be made to the identification result "primary pulmonary cancer" and/or the identification reason "high tumor marker, and presence of nodular shadow", the operator selects button B2. When button B2 is selected by the operator on the communication terminal 40, the communication terminal 40 transmits to the diagnosis support apparatus 10 an instruction to change the identification result shown in area A1 and/or the identification reason shown in area A2. After selecting button B2, the operator inputs a change to the shown identification result and/or identification reason.

After the instruction to change the identification result and/or identification reason is received, and a change to the shown identification result and/or identification reason is input by the operator (No in step S55 and Yes in step S511), the processing circuitry 11 of the diagnosis support apparatus 10 updates the identification result in area A1 and/or identification reason in area A2 with input information (step S512). After updating the identification result in area A1 and/or identification reason in area A2, the processing circuitry 11 terminates the processing.

When determining that the identification result in area A1 and identification reason in area A2 shown in FIG. 7 are acceptable, the operator selects button B3 on the communication terminal 40. When button B3 is selected by the operator on the communication terminal 40, the communication terminal 40 transmits to the diagnosis support apparatus 10 an instruction to accept the identification result in area A1 and the identification reason in area A2.

Upon receipt of the instruction to accept the identification result and the identification reason (No in step S55 and No in step S511), the processing circuitry 11 of the diagnosis support apparatus 10 terminates the processing. The accepted identification result and identification reason are used in, for example, preparation of an interpretation report, preparation of a description for the patient, or preparation of a recommendation letter for another hospital.

In the present embodiment, the processing circuitry 11 of the diagnosis support apparatus 10 uses the identification function 112 to execute identification processing by using medical information as an input and thereby output an identification result and an identification reason for providing the result, as described above. In response to an instruction to reject the identification reason, the processing circuitry 11 uses the modification function 113 to change identification processing so that the rejected identification reason is not output. Then, the processing circuitry 11 uses the re-identification function 114 to execute modified identification processing by using medical information as an input and thereby output an identification result and an identification reason for providing the result. Accordingly, the doctor, who is the operator, can obtain an identification reason reflecting their own determination, and an identification result based on the reason. Namely, the doctor can provide feedback on the identification process, not the result itself.

In the present embodiment, the processing circuitry 11 executes identification result by further using information not included in the medical information as an input and thereby outputs an identification result and an identification reason for providing the result. This improves the accuracy of identification processing using trained models.

Figure 11:
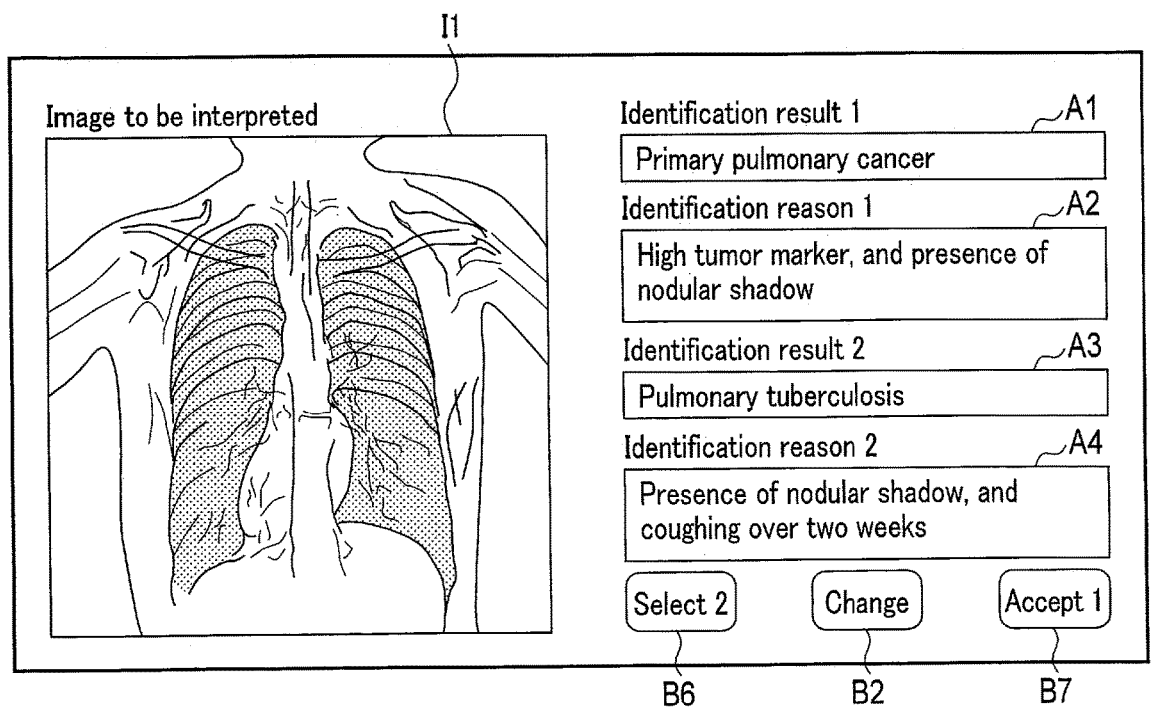
FIG. 11 is a diagram showing a screen displaying a plurality of identification results and a plurality of identification reasons on the communication terminal shown in FIG. 1.

Described in the above embodiment as an example is the case where one identification result and one identification reason are displayed as shown in, for example, FIGS. 7 and 10. However, the embodiment is not limited to this. A plurality of identification results and a plurality of identification reasons may be displayed. FIG. 11 is a schematic diagram showing a display example of the communication terminal 40 of the case where a plurality of identification results and a plurality of identification reasons are displayed. In FIG. 11, two most probable identification results and two identification reasons for providing the respective results are shown.

At this time, trained model 121-1$a$ stored in the memory 12 of the diagnosis support apparatus 10 performs machine learning based on, for example, training data consisting of inputs of identification results output from trained models 121-2 to 121-N and identification reasons for providing the results and correct outputs of a determined disease name and a reason for the diagnosis. Trained model 121-1$a$ is generated to output, for example, a first candidate identification result and identification reason and a second candidate identification result and identification reason in response to input of identification results and identification reasons output from trained models 121-2 to 121-N.

In FIG. 11, buttons B6, B2, and B7 are shown as a GUI. Button B6 is a button for rejecting the identification reason shown in area A2 and accepting the identification reason shown in area A4. Button B7 is a button for accepting the identification result shown in area A1 and the identification reason shown in area A2.

When the operator determines that the identification reason shown in area A4 is closer to the reason envisaged by the operator than the identification reason shown in area A2, the operator selects button B6 on the communication terminal 40. For example, when the operator determines that the reason "presence of nodular shadow, and coughing over two weeks" shown in area A4 is closer to the reason envisaged by the operator than the reason "high tumor marker, and presence of nodular shadow" shown in area A2, the operator selects button B6. When button B6 is selected by the operator on the communication terminal 40, the communication terminal 40 transmits to the diagnosis support apparatus 10 an instruction to reject the identification reason shown in area A2 and accept the identification reason shown in area A4.

Upon receipt of the instruction to reject the first candidate identification reason and accept the second candidate identification reason from the communication terminal 40, the processing circuitry 11 of the diagnosis support apparatus 10 modifies the algorithm of the trained models based on the instruction. For example, the processing circuitry 11 refrains from executing identification processing using the trained model that has output the first candidate identification reason. The processing circuitry 11 performs identification processing again by using the trained models after algorithm modification.

Alternatively, the processing circuitry 11 may raise the priority of the identification result and identification reason output from the trained model that has output the same identification reason as the second candidate identification reason accepted by the operator. By causing the communication terminal 40 to display a plurality of identification results and identification reasons as described above, the operator can provide feedback on the identification process by comparing the first candidate identification reason with the second candidate identification reason.

Described in the above embodiment as an example of processing performed when modifying the algorithm is the case of refraining from executing identification processing using one trained model. However, the embodiment is not limited to this. To modify the algorithm, for example, new trained model 121-(N+1) may be added. The added trained model 121-(N+1) may be a trained model trained by using, for example, training data different from training data used for machine learning of trained models 121-2 to 121-N. Accordingly, an identification result different from those output from trained models 121-2 to 121-N are output from trained model 121-(N+1).

Figure 12:
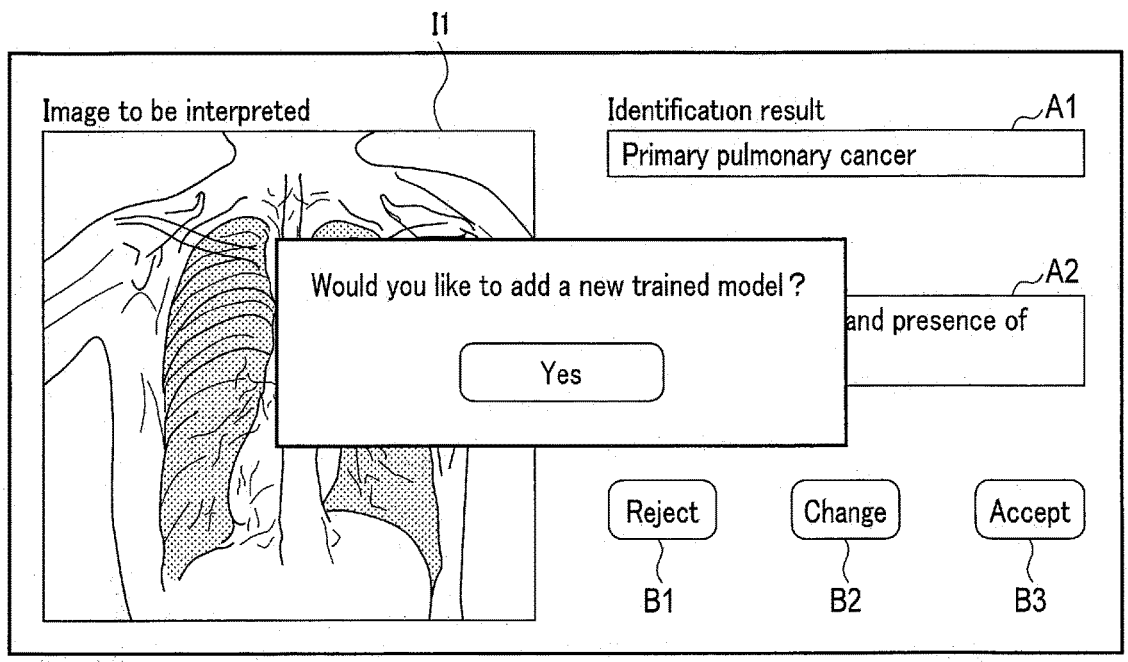
FIG. 12 is a diagram showing a screen to receive a selection of whether to add a new trained model on the communication terminal shown in FIG. 1.

For example, when reject button B1 shown in FIG. 7 is selected by the operator, the processing circuitry 11 of the diagnosis support apparatus 10 causes the communication terminal 40 to display a screen to receive a selection of whether or not to add a new trained model. FIG. 12 is a schematic diagram showing an example of the screen to receive a selection of whether to add a new trained model. When the operator selects "Yes", the processing circuitry 11 executes the modification function 113.

Figure 13:
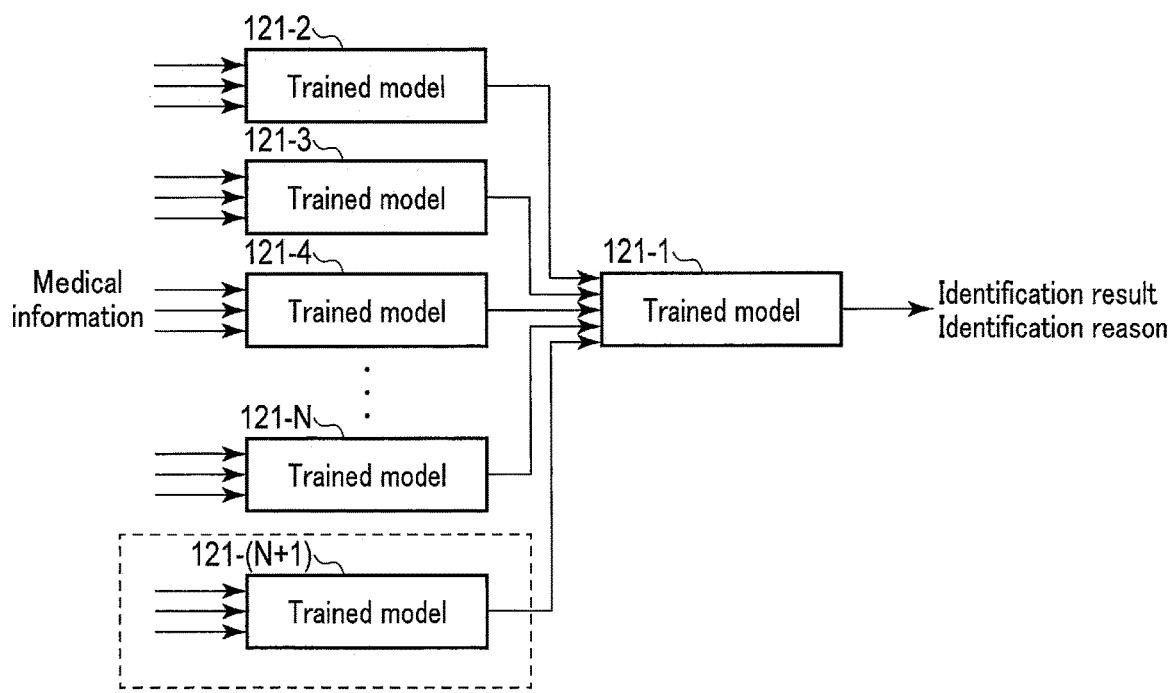
FIG. 13 is a diagram showing a configuration of the identification device of when a new trained model is added.

By executing the modification function 113, the processing circuitry 11 modifies the algorithm of the trained models 121-1 to 121-N. For example, the processing circuitry 11 adds trained model 121-(N+1) to cause identification result R (N+1) 1 and identification reason R (N+1) 2 output from trained model 121-(N+1) to be input to trained model 121-1. FIG. 13 is a schematic diagram showing a configuration of the identification device of when trained model 121-(N+1) is added. Trained model 121-1 in this case is generated based on the assumption that trained model 121-(N+1) would be added. The processing circuitry 11 performs identification processing again by using the trained models after algorithm modification. Accordingly, the processing circuitry 11 enables the operator to make determination in consideration of the identification result and identification reason output from the newly-added trained model.

Described in the above embodiment as an example is the case where identification processing is performed by using a plurality of trained models 121-1 to 121-N. However, the embodiment is not limited to this. The processing circuitry 11 of the diagnosis support apparatus 10 may perform identification processing, for example, by using one trained model. The trained model used in this case is generated by utilizing a machine learning algorithm, such as discrimination analysis, logistic regression, a support vector machine, a neural network, Randomized Trees, or a subspace method.

For example, when an instruction to start identification processing for a designated patient is input by an operator who operates the communication terminal 40, the processing circuitry 11 executes the information acquisition function 111, and reads medical information on the patient designated by the operator from the electronic health record system 20 and medical image management system 30. After reading the medical information, the processing circuitry 11 executes the identification function 112, and inputs the read medical information into the trained model, thereby outputting an identification result and an identification reason for providing the result.

When the identification result and identification reason are output, the processing circuitry 11 causes the communication terminal 40 to display, for example, the screen shown in FIG. 7. When the reject button B1 shown in FIG. 7 is selected, and the re-computation button 135 shown in FIG. 8 is selected, the processing circuitry 11 executes the modification function 113.

Figure 14:
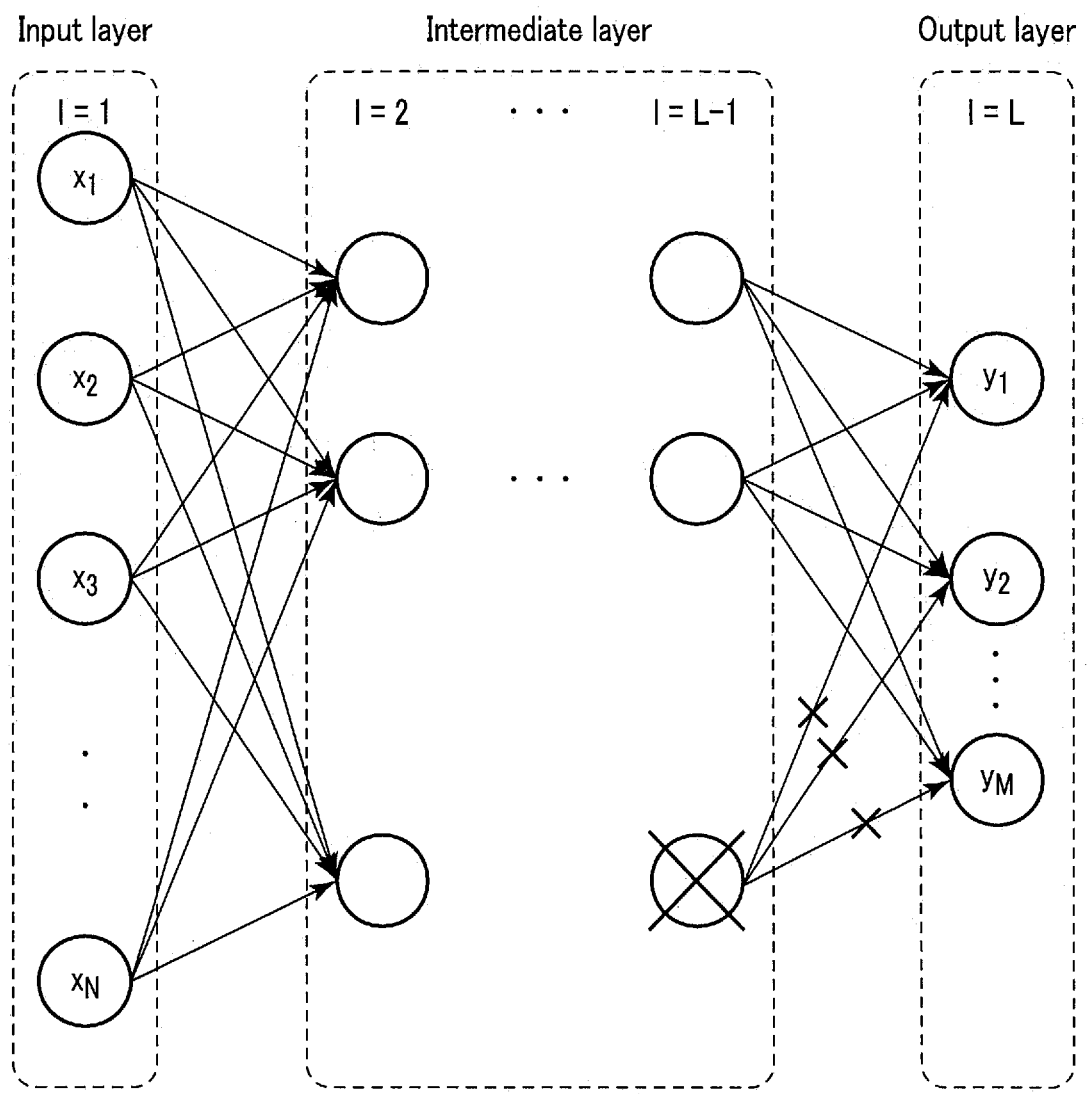
FIG. 14 is a diagram showing another example of the modification of the algorithm.

By executing the modification function 113, the processing circuitry 11 modifies the algorithm of the trained model to exclude the identification reason rejected by the operator. For example, when the trained model is a trained model generated by using a neural network, the processing circuitry 11 sets a trained model generated by deleting the node relating to the rejected identification reason as shown in FIG. 14. Namely, a trained model in which at least one parameter in the intermediate layer is changed is set. The processing circuitry 11 performs identification processing by using the newly-set trained model.

Figure 15:
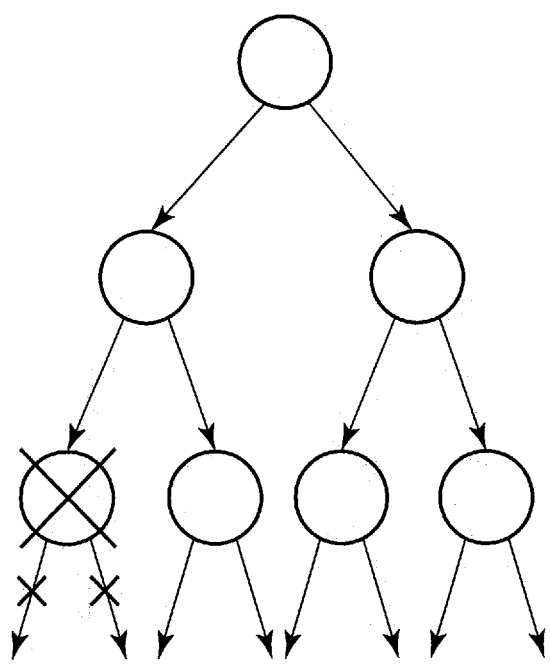
FIG. 15 is a diagram showing another example of the modification of the algorithm.

When the trained model is a trained model generated by using a decision tree, the processing circuitry 11 deletes branches relating to the rejected identification reason as shown in FIG. 15. The processing circuitry 11 performs identification processing by using the newly-set trained model.

Described in the above embodiment as an example is the case where a disease name, a malignancy grade of the disease, etc. are output as identification results by the identification function 112 of the processing circuitry 11. However, the embodiment is not limited to this. For example, an image processing result may be output as an identification result.

For example, when an instruction to start identification processing for a designated patient is input by an operator who operates the communication terminal 40, the processing circuitry 11 executes the information acquisition function ill, and reads medical image data on the patient designated by the operator from the medical image management system 30. After reading the medical image data, the processing circuitry 11 executes the identification function 112, and inputs the read X-ray image data into the trained model, thereby outputting an image processing result and a display reason for performing the image processing.

When the image processing result and display reason are output, the processing circuitry 11 causes the communication terminal 40 to display, for example, the screen shown in FIG. 16. In the example shown in FIG. 16, medical image I1 after image processing is displayed on the left side, and area A5 showing a display reason is displayed on the right side. More specifically, in FIG. 16, an image enhancing a stent is shown as medical image I1, and "stent included and thus enhanced" is shown in area A5 as a display reason. Below area A5, buttons B1 to B3 are displayed as a GUI.

Let us assume that the operator ascertained the screen shown in FIG. 16 notices that objects desired to be observed, for example, blood vessels are not clearly shown in the screen. Area A5 shows "stent included and thus enhanced" as a display reason. Therefore, the operator selects the reject button B1, and transmits to the diagnosis support apparatus 10 an instruction to reject the display reason shown in area A5. Upon receipt of the instruction to reject the display reason, the processing circuitry 11 of the diagnosis support apparatus 10 executes the modification function 113.

By executing the modification function 113, the processing circuitry 11 modifies the algorithm of the trained models to exclude the display reason rejected by the operator. For example, the processing circuitry 11 refrains from executing identification processing using the trained model that has output the rejected display reason.

After modifying the algorithm of the trained models, the processing circuitry 11 executes the re-identification function 114. By executing the re-identification function 114, the processing circuitry 11 inputs medical image data into the trained models after algorithm modification, and re-outputs an image processing result and a display reason. The processing circuitry causes the communication terminal 40 to display the image processing result and the display reason. FIG. 17 is a schematic diagram showing an example of the image re-displayed on the communication terminal 40. In the example shown in FIG. 17, medical image I1 after re-image processing is displayed, and the re-output display reason is shown in area A5. More specifically, in FIG. 17, an image enhancing blood vessels is displayed as medical image I1, and "blood vessels enhanced" is shown in area A5 as a display reason. Accordingly, a display reason different from the display reason rejected by the operator is displayed, and medical image I1 based on the display reason is displayed in parallel.

According to at least one embodiment described above, a more probable identification reason, of which the doctor can be convinced, can be output together with an identification result based on the reason. The coexistence with AI leads to highly reliable determination based on a merger between findings of the doctor and findings of AI.

The term "processor" used in the above description of the embodiment means, for example, a central processing unit (CPU), a graphics processing unit (GPU), or circuitry such as an application specific integrated circuit (ASIC), or a programmable logic device (e.g., a simple programmable logic device (SPLD), a complex programmable logic device (CPLD), or a field programmable gate array (FPGA)). The processor realizes a function by reading and executing a program stored in memory circuitry. Instead of storing a program in memory circuitry, a program may be directly integrated into circuitry of a processor. In this case, the processor realizes functions by reading and executing programs integrated in the circuitry. Each processor of the above embodiment is not necessarily configured as a single circuit, but may be configured by a combination of a plurality of independent circuits to realize its functions. Furthermore, a plurality of constituent elements in the above embodiment may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A diagnosis support apparatus, comprising:
a memory storing a trained model; and
processing circuitry configured to
execute identification processing with the trained model by using medical information, including medical image data, as an input to output a first identification result and a first identification reason for providing the first identification result;
in response to an instruction to reject the first identification reason, modify the trained model to perform modified identification processing by causing the trained model to refrain from outputting the first identification reason;
execute the modified identification processing with the modified trained model by using the medical information, including the medical image data, as an input to output a second identification result and a second identification reason for providing the second identification result, the second identification reason being different from the first identification reason; and
output the second identification result and the second identification reason as part of at least one of an interpretation report, a description for a patient, and a medical recommendation,
wherein the processing circuitry is further configured to
output a third identification result and a third identification reason for providing the third identification result; and
in response to an instruction to both reject the first identification reason and accept the third identification reason, modify the trained model to perform modified identification processing by causing the trained model to refrain from outputting the first identification reason.

2. The diagnosis support apparatus according to claim 1, wherein the processing circuitry is further configured to execute the identification processing by further using information not included in the medical information as an input to output the third identification result and the third identification reason for providing the third identification result.

3. The diagnosis support apparatus according to claim 1, wherein the processing circuitry is further configured to add a new trained model.

4. A diagnosis support system, comprising:
a memory storing a trained model; and
processing circuitry configured to
execute identification processing with the trained model by using medical information, including medical image data, as an input to output a first identification result and a first identification reason for providing the first identification result;
modify the trained model to perform modified identification processing by causing the trained model to refrain from outputting the first identification reason in response to an instruction to reject the first identification reason;
execute the modified identification processing with the modified trained model by using the medical information, including the medical image data, as an input to output a second identification result and a second identification reason for providing the second identification result, the second identification reason being different from the first identification reason; and
output the second identification result and the second identification reason as part of at least one of an interpretation report, a description for a patient, and a medical recommendation,
wherein the processing circuitry is further configured to
output a third identification result and a third identification reason for providing the third identification result; and
in response to an instruction to both reject the first identification reason and accept the third identification reason, modify the trained model to perform modified identification processing by causing the trained model to refrain from outputting the first identification reason.

5. A diagnosis support method, comprising:
storing a trained model in a memory;
executing identification processing with the trained model by using medical information, including medical image data, as an input to output a first identification result and a first identification reason for providing the first identification result;
receiving an instruction to reject the first identification reason;
modifying the trained model to perform modified identification processing by causing the trained model to refrain from outputting the first identification reason in response to the instruction to reject the first identification reason;
executing the modified identification processing with the modified trained model by using the medical information, including the medical image data, as an input to output a second identification result and a second identification reason for providing the second identification result, the second identification reason being different from the first identification reason; and
outputting the second identification result and the second identification reason as part of at least one of an interpretation report, a description for a patient, and a medical recommendation,
wherein the method further comprises
outputting a third identification result and a third identification reason for providing the third identification result; and
in response to an instruction to both reject the first identification reason and accept the third identification reason, modifying the trained model to perform modified identification processing by causing the trained model to refrain from outputting the first identification reason.

6. A non-transitory storage medium storing a program that, when executed by processing circuitry, causes the processing circuitry to:
execute identification processing with a trained model stored in a memory by using medical information, including medical image data, as an input to output a first identification result and a first identification reason for providing the first identification result;
modify the trained model to perform modified identification processing by causing the trained model to refrain from outputting the first identification reason in response to an instruction to reject the first identification reason;
execute the modified identification processing with the modified trained model by using the medical information, including the medical image data, as an input to output a second identification result and a second identification reason for providing the second identification result, the second identification reason being different from the first identification reason; and
output the second identification result and the second identification reason as part of at least one of an interpretation report, a description for a patient, and a medical recommendation,
wherein the program further causes the processing circuitry to:
output a third identification result and a third identification reason for providing the third identification result, and
in response to an instruction to both reject the first identification reason and accept the third identification reason, modify the trained model to perform modified identification processing by causing the trained model to refrain from outputting the first identification reason.

7. The diagnosis support apparatus according to claim 1, wherein the processing circuitry is further configured to output the interpretation report.

8. The diagnosis support apparatus according to claim 1, wherein the processing circuitry is further configured to output the description for the patient.

9. The diagnosis support apparatus according to claim 1, wherein the processing circuitry is further configured to output the medical recommendation.

10. The diagnosis support apparatus according to claim 1, wherein the trained model is a trained neural network.

11. The diagnosis support apparatus according to claim 10, wherein the processing circuitry is further configured to modify the trained neural network by deleting a node relating to the rejected first identification reason.

12. The diagnosis support apparatus of claim 1, wherein the processing circuitry is further configured to receive the medical image data, which was obtained by a scan of a patient using a medical imaging apparatus.

13. The diagnosis support apparatus of claim 1, wherein the processing circuitry is further configured to receive the medical information, which further includes non-image data.

14. The diagnosis support apparatus of claim 1, wherein the processing circuitry is further configured output the first identification result, which indicates presence or absence of a medical abnormality, and the first identification reason, which indicates supporting medical indicators for the present or absence of the medical abnormality.

* * * * *